US010617469B2

(12) United States Patent
Palero et al.

(10) Patent No.: US 10,617,469 B2
(45) Date of Patent: Apr. 14, 2020

(54) SKIN TREATMENT DEVICE PROVIDING OPTICAL COUPLING TO SKIN TISSUE (71) Applicant: KONINKLIJKE PHILIPS N.V., Eindhoven (NL)

(72) Inventors: Jonathan Alambra Palero, Eindhoven (NL); Martin Jurna, Eindhoven (NL); Babu Varghese, Eindhoven (NL); Margaret Ruth Horton, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 836 days.

(21) Appl. No.: 15/033,807

(22) PCT Filed: Nov. 6, 2014

(86) PCT No.: PCT/EP2014/073858
§ 371 (c)(1),
(2) Date: May 2, 2016

(87) PCT Pub. No.: WO2015/067676
PCT Pub. Date: May 14, 2015

(65) Prior Publication Data
US 2016/0249983 A1  Sep. 1, 2016

(30) Foreign Application Priority Data

Nov. 7, 2013 (EP) ..................... 13191864

(51) Int. Cl.
*A61B 18/20* (2006.01)
*A61B 90/00* (2016.01)
(Continued)

(52) U.S. Cl.
CPC .. *A61B 18/203* (2013.01); *A61B 2017/00026* (2013.01); *A61B 2017/00057* (2013.01);
(Continued)

(58) Field of Classification Search
CPC ........ A61B 18/203; A61B 2017/00026; A61B 2017/00057; A61B 2018/0047;
(Continued)

(56) References Cited

U.S. PATENT DOCUMENTS

2002/0058953 A1* 5/2002 Gruzdev ............ A61B 5/15134
606/131
2008/0172047 A1* 7/2008 Altshuler ............... A61B 5/441
606/9
(Continued)

FOREIGN PATENT DOCUMENTS

WO 2008001284 A2 1/2008
WO 2013053367 A1 4/2013

OTHER PUBLICATIONS

A.A.J. Benschop & A.J. Garenfeld, "Saturnus Shaving System", Nat. Lab Technical Note NR. 302/93, Jan. 8, 1998. pp. 1-56.
(Continued)

*Primary Examiner* — Michael W Kahelin
*Assistant Examiner* — Vynn V Huh (57) ABSTRACT

The invention provides a non-invasive skin treatment device (200) comprising: a light source (10) constructed for emitting treatment light (15), an optical system (20) constructed for focusing the treatment light along an optical axis (OA) to a focus position (320) inside the skin tissue (300), and an indenter (30) comprising a skin contact surface (34) having an aperture (A1) at a distance from the optical system for allowing the treatment light to be focused through the aperture into the skin tissue. The indenter is configured and constructed for generating, in a cross-section of the aperture taken along the optical axis and along a cross-section direction wherein the aperture has a width dimension, a maximally curved protrusion of skin tissue freely protruding through the aperture towards the optical system by pressing the indenter against the skin surface of a specific skin type (Continued)

with a pressure exceeding a predefined pressure, a skin surface of said maximally curved protrusion having a radius of curvature (RC) at an intersection with the optical axis. The optical system is configured and constructed for generating a focused beam of the treatment light having, in said cross-section of the aperture at said intersection, a wave front with a radius of curvature ranging between 75% and 125% of said radius of curvature (RC) of the skin surface of said maximally curved protrusion.

16 Claims, 6 Drawing Sheets

(51) Int. Cl.
  *A61B 18/00*     (2006.01)
  *A61B 17/00*     (2006.01)
(52) U.S. Cl.
  CPC ............... *A61B 2018/0047* (2013.01); *A61B 2018/00773* (2013.01); *A61B 2018/20355* (2017.05); *A61B 2018/20361* (2017.05); *A61B 2090/065* (2016.02); *A61B 2562/0247* (2013.01)
(58) Field of Classification Search
  CPC .... A61B 2018/00773; A61B 2018/202; A61B 2090/065; A61B 2562/0247
  USPC .................................................. 607/88–94
  See application file for complete search history.

(56) References Cited

U.S. PATENT DOCUMENTS

| | | | |
|---|---|---|---|
| 2008/0221649 A1 | 9/2008 | Echague | |
| 2010/0016761 A1* | 1/2010 | Rosenberg | A61B 18/14 601/2 |
| 2011/0102818 A1 | 5/2011 | Lee | |

OTHER PUBLICATIONS

D.Brokken, "Towards the Prediction of Non-Static Skin Doming", Nat. Lab Technical Note 2001/108, Issue Date Mar. 2001. pp. 1-38.
Marion Geerligs, "Skin Layer Mechanics" Koninklijke Philips Electroncis N.V. 2009. pp. 1-122.
F.M. Kendriks, "Mechanical Behaviour of Human Skin in Vivo", Koninklijke Philips Electronics N.V. 2001. pp. 1-52.
E.J.A Kosters, F. Fraij, "Measurement of Skin Doming Replica's". Nat.Lab. Technical Note NR. 101/92, Philips Electronics N..V. 192. pp. 1-32.
Yhong-Ping Zheng, : An Ultrasound Indentation System for Biomechanical Properties Assessment of Soft Tissues In-Vivo, Biomedical Engineering, IEEE, vol. 43, Issue 9. Sep. 1996.

* cited by examiner

SKIN TREATMENT DEVICE PROVIDING OPTICAL COUPLING TO SKIN TISSUE

This application is the U.S. National Phase application under 35 U.S.C. § 371 of International Application No. PCT/EP2014/073858, filed on Nov. 6, 2014, which claims the benefit of International Application No. 13191864.1 filed on Nov. 7, 2013. These applications are hereby incorporated by reference herein.

FIELD OF THE INVENTION

The invention generally relates to the treatment of skin using light, and more particularly to a skin treatment device providing optical coupling to skin tissue.

BACKGROUND OF THE INVENTION

The desire to maintain a youthful appearance by preventing or reducing wrinkles in the skin is an important issue in human society. Many techniques have been designed to achieve the above issue. One of the techniques, e.g., known from the published international patent application WO 2008/001284 A2, is to create a focal spot in a dermis layer of the skin to be treated. Said WO application discloses a skin treatment device with a laser source and focusing optics. The device emits a laser beam. The power of the laser is selected such that Laser Induced Optical Breakdown (LIOB) affects the skin in order to stimulate re-growth of skin tissue and reduce wrinkles. This LIOB is based on strong non-linear absorption of the laser light by the skin tissue, which occurs above a certain threshold value for the power density of the laser light.

In addition to LIOB, also other light-based treatment processes are known, such as fractional photothermolysis to create microscopic thermal lesions in the epidermis or dermis of the skin tissue to stimulate re-growth of the damaged skin tissue to rejuvenate the skin tissue and reduce wrinkles Rejuvenation processes through light-based treatment inside the skin tissue (such as said laser induced optical breakdown and fractional photothermolysis) require high photon densities in localized regions in the tissue. When light propagates through the skin tissue, absorption, scattering and deformation of wave fronts often result in a relatively broad distribution of light at the focus position and a distribution of the light energy over a relatively broad focal spot. Because of the high intensity requirement and the spreading of the light over a relatively large focal spot, the overall intensity of the treatment light necessary to perform the light-based treatment of skin tissue is increased. This typically increases the requirements to be met by the light sources used in such skin treatment devices, causing said skin treatment devices to be more expensive, and the increased overall intensity of the treatment light increases possible damage to skin tissue surrounding the treatment position, which is also undesirable.

Consequently, in the known skin treatment devices the quality of focusing the treatment light from the light source to the focus position is not optimal, which requires the known skin treatment devices to use an excess of light energy to produce this light-based treatment process.

SUMMARY OF THE INVENTION

An object of the invention is to provide a more effective light delivery inside the skin tissue for skin treatment devices.

The object is achieved according to the invention by a skin treatment device comprising:

a light source constructed for emitting treatment light, an optical system constructed for focusing the treatment light along an optical axis to a focus position inside the skin tissue, and an indenter comprising a skin contact surface having an aperture at a distance from the optical system for allowing the treatment light to be focused through the aperture into the skin tissue, the indenter and the aperture being configured and constructed for generating, in a cross-section of the aperture taken along the optical axis and along a cross-section direction wherein the aperture has a width dimension, a maximally curved protrusion of skin tissue freely protruding through the aperture towards the optical system when the indenter is pressed against the skin surface of a specific skin type with a pressure exceeding a predefined pressure above which for the specific skin type the freely protruding curved protrusion remains constant, a skin surface of said maximally curved protrusion having a radius of curvature at an intersection with the optical axis, the optical system being configured and constructed for generating a focused beam of the treatment light having, in said cross-section of the aperture at said intersection, a wave front with a radius of curvature ranging between 75% and 125% of said radius of curvature of the skin surface of said maximally curved protrusion.

The invention is based on the insight that, when pressing an indenter having a specific aperture against the skin surface, a skin protrusion occurs in the aperture as a result of the deformation of the skin. This skin protrusion freely protrudes into the aperture towards the optical system. The inventors have found that a curvature of this freely protruding protrusion mainly depends on a dimension of the aperture, while the characteristics of the freely protruding protrusion, such as protrusion height from the skin surface and the curvature of the protrusion, remain relatively constant as long as the pressure with which the indenter is pressed against the skin surface exceeds a predefined pressure. So, when the pressure with which the indenter is pressed against the skin exceeds the predefined pressure, the curvature which occurs in the aperture is at a maximum, i.e. forming a maximally curved protrusion having a minimal radius of curvature at its skin surface, and is substantially maintained when the pressure is further increased. In the context of the invention, "freely" protruding means that, under the influence of the pressure with which the indenter is pressed against the skin surface, the skin is allowed to freely deform into the aperture without experiencing any resistance, in particular without coming into contact with or abutting against any objects. The inventors have further realized that the optical system may be configured to generate a focused beam of treatment light which has a wave front, at the surface of the maximally curved protrusion, with a radius of curvature ranging between 75% and 125% of the radius of curvature of the skin surface of said maximally curved protrusion. In this way, the wave front nearly or fully coincides with or matches the maximally curved protrusion, which improves the quality with which the beam of treatment light is focused into the skin tissue by the optical system of the skin treatment device. This improvement of the focusing quality is the result of a strong reduction of the spherical aberration caused by the fact that, due to said substantial or full coinciding of the wave front and the skin surface of the skin protrusion, the light rays of the beam propagate perpendicularly or nearly perpendicularly to the skin surface. As a result, the focus is better defined and the focal spot may be smaller, causing less spreading of the light energy and reducing the overall power required to perform the light-based skin treatment.

A height of the protrusion is defined as the distance over which the protrusion enters the aperture, measured from the skin contact surface of the indenter. This height of the protrusion, together with the curvature of the skin surface of the protrusion, is important to ensure that the curvature of the wave front at the surface of the protrusion substantially corresponds to the curvature of the protrusion. However, the inventors have found that, in addition to the curvature, also the height of the protrusion becomes substantially constant when the pressure with which the indenter is pressed against the skin surface exceeds the predefined pressure. This occurs especially at width dimensions of the cross-section of the aperture below 5 millimeters, and preferably even below 3 millimeters. For example, the predefined pressure for an aperture having a dimension of approximately 2 millimeters is around 1.43 Newton per square centimeter, which is relatively low. Therefore, when the skin treatment device is used, the skin treatment device is typically pressed against the skin surface, for example, at a nominal pressure. In the current example, using a nominal pressure above 1.43 Newton per square centimeter would cause the height of the protrusion and the radius of the curvature of the surface of the protrusion to become constant, i.e. would cause the protrusion to become maximal. In this example, with the pressure above 1.43 Newton per square centimeter, the curved skin protrusion is a maximally curved protrusion, i.e. having a minimal radius of curvature at its surface. Correctly adapting the optical system to focus the treatment light allows generating a radius of curvature of the wave front at the location of the surface of the maximally curved protrusion, and in particular at an intersection of said surface with the optical axis of the light beam, which ranges between 75% and 125% of the radius of curvature of the skin surface of the maximally curved protrusion. A look-up table may, for example, be used to indicate, for a number of specific skin types, the preferred width dimension of the aperture and the minimal predefined pressure. The fact that the height of the maximally curved skin protrusion is substantially constant when pressing the indenter against the skin surface with a pressure exceeding the predefined pressure, enables controlling the position of the surface of the skin protrusion relative to the focusing elements of the optical system, such that the radius of curvature of the wave front of the focused treatment light corresponds, within the prescribed tolerance range, to the radius of curvature of the skin surface of the maximally curved protrusion. In such a situation, substantially all treatment light impinges perpendicularly or nearly perpendicularly on the skin surface, which significantly reduces the spherical aberration of the treatment light focused into the skin tissue.

In an embodiment of the skin treatment device, the width dimension of the aperture is less than 2 millimeters. As mentioned hereinbefore, at relatively small width dimensions of the aperture, the predefined pressure required to achieve the maximally curved protrusion is relatively low. As such, selecting the width dimension of the cross-section of the aperture to be less than 2 millimeters ensures that, in normal use, the usual nominal pressure with which the skin treatment device is pressed against the skin surface already exceeds the predefined pressure. However, there is another reason why the cross-sectional dimension of the aperture is preferably less than 2 millimeters. The wavelength of the treatment light typically used in light-based treatment of the skin tissue is around 1064 nanometer. This wavelength has a relatively large penetration depth into the skin tissue. However, even light having a wavelength of 1064 nanometer has an effective penetration depth of less than 2 millimeter into the skin tissue. In the case of an aperture of 2 millimeters, the radius of curvature of the skin surface of said maximally curved protrusion requires, when the indenter is applied against the skin tissue of a human face, the optical system to focus the light approximately 2.4 millimeter into the skin tissue in order to have the radius of curvature of the wave front substantially coincide with the radius of curvature of the maximally curved protrusion. This would already exceed the maximum penetration depth of the used treatment light into the skin. So, using the skin treatment device with a larger aperture of the indenter would require even deeper penetration of the treatment light into the skin tissue, which would require the use of other, non-preferred, treatment light in the light-based skin treatment. Accordingly, in an embodiment of the skin treatment device, the predefined pressure is 1.43 Newtons per square centimeter. In a further embodiment of the skin treatment device, the radius of curvature of the wave front ranges between 95% and 105% of said radius of curvature of the skin surface of the maximally curved protrusion. Such a lower tolerance results in better matching of the curvature of the wave front and the curvature of the maximally curved protrusion as well as a stronger reduction of wave front aberrations due to the focusing into the skin tissue.

In an embodiment of the skin treatment device, the indenter is removably attached to the skin treatment device and is replaceable by a further indenter having a further aperture different from the aperture. Using a further aperture having a different width dimension may be beneficial when the skin treatment device is used for a different predefined skin type. The maximally curved protrusion occurs due to the viscoelastic properties of the skin tissue. These viscoelastic properties of the skin tissue may vary for different skin types. Different skin types include genetic differences between skin types and age differences between skin types at substantially the same location on the human or animal body. Different skin types also include differences of the skin types at different locations of the human or animal body. When applying the skin treatment device, the viscoelastic properties of the skin tissue determine the maximally curved protrusion that is generated by applying the indenter against the skin surface. Thus, when for example changing from light-based treatment of the facial skin to light-based treatment of other parts of the body, the indenter may need to be replaced by the further indenter to ensure that the maximally curved protrusion has a radius of curvature ranging between 75% and 125% of the radius of the wave front of the treatment light as focused by the optical system. Alternatively, an adjustable aperture may be used having an adjustable width dimension instead of a replaceable indenter to adjust the width dimension of the cross-section of the aperture in dependence on the skin type for which the light-based treatment is to be performed.

In an embodiment of the skin treatment device, a dimension of the aperture in a direction transverse to the cross-section direction of the aperture is larger than 2 millimeters. In this embodiment, the aperture is for example an elongated aperture which may, for example, be used when the optical system generates an elongated focus. Alternatively, the elongated aperture may be used in combination with an array of focus positions inside the skin tissue illuminated simultaneously or sequentially by the skin treatment device according to the invention. In such an embodiment, the radius of curvature of the maximally curved protrusion matches the radius of curvature of the plurality of wave fronts generated by the light source in only one direction, i.e. only in a cross-sectional plane of the aperture taken along the optical axis and along the cross-section direction wherein the aperture has its width dimension. Although this is not an ideal situation, this matching of the radius of curvature of the wave front and the radius of curvature of the maximally curved protrusion in only one direction already improves the overall focusing quality of the treatment light into the skin tissue such that a reduction of the spherical aberration is observed. This already reduces the overall intensity requirement of the treatment light required for the light-based treatment of skin tissue.

In an embodiment of the skin treatment device, the optical system is configured and constructed to generate a plurality of spatially separate focusing positions inside the skin tissue, and the indenter comprises a plurality of apertures each associated with a respective one of said plurality of focusing positions and each configured and constructed for generating a maximally curved protrusion of the skin tissue, the optical system being configured and constructed for generating a plurality of focused beams of the treatment light each having, in said cross-section of the associated aperture at said intersection, a wave front with a radius of curvature ranging between 75% and 125% of said radius of curvature of the skin surface of said maximally curved protrusion. A benefit of this embodiment is that multiple positions inside the skin tissue may be treated at the same time by the skin treatment device. Especially when the width dimension of the cross-section of the apertures is less than 2 millimeters, the skin treatment device may relatively easily comprise a plurality of apertures to ensure this simultaneous treatment. The plurality of apertures may be arranged in a one-dimensional array or a two-dimensional array. Furthermore, the skin treatment device may comprise different indenters which have different arrays of apertures, wherein a distance between two neighboring apertures is different for the different indenters. In such an embodiment, a user may choose a density of the spatially separated focusing positions or treatment positions inside the skin tissue, and differences in densities of the focusing positions or treatment positions may be preferred for some specific light-based treatments of the skin tissue.

In an embodiment of the skin treatment device, the indenter is attached to the skin treatment device via a resilient element. Using a resilient element ensures that the pressure with which the indenter is applied to the surface of the skin exceeds the predefined pressure. For example, the skin treatment device should be pressed against the skin surface until, for example, a length of the resilient element is at least partially reduced due to the applied pressure. If this happens, the applied pressure exceeds the predefined pressure with which the indenter has to pressed against the skin surface to create the maximally curved skin protrusion. A further benefit when using such a resilient element is that it ensures that always substantially the same pressure is applied during the treatment using the skin treatment device. For example, when the resilient element is a spring, the pressure may be increased until the spring compresses, but not until the spring is completely compressed. It is thus ensured that the pressure with which the indenter is applied to the skin surface is substantially the same at different locations on the human or animal body.

In an alternative embodiment, the skin treatment device comprises a pressure sensor for measuring the pressure with which the indenter, in use, is pressed against the skin surface, and a control circuit configured to control the light source to emit the treatment light only when the pressure measured by the pressure sensor exceeds the predefined pressure. In this arrangement, the pressure sensor may act as a kind of activation button, wherein, as soon as the sensed pressure exceeds the predefined pressure, the skin treatment device may activate the light source to start the treatment. Alternatively, the pressure sensor may provide a signal to the user, e.g. audible or visible, as soon as the sensed pressure exceeds the predefined pressure such that the light-based treatment may be initiated. Such a pressure sensor may, for example, be a piezo-electric sensor, but any other pressure sensor may also be used. A further benefit of having the pressure sensor in the skin treatment device according to the invention is that different predefined pressure levels may be used for different indenters of the skin treatment device. The pressure sensor may be manually set to a different level when using a different indenter or when using the indenter on a different skin type. Alternatively, the skin treatment device may recognize the indenter and use a different predefined pressure level automatically, for example, through looking up the corresponding or required predefined pressure level in a further look-up table (for example, stored somewhere in the skin treatment device) indicating the required pressure levels for different skin types and different indenters.

In an embodiment of the skin treatment device, the skin treatment device further comprises a curvature sensor for sensing a position and/or a curvature of the maximally curved protrusion at the intersection with the optical axis. Such a curvature sensor may be used to adapt the position of the focus generated by the optical system of the skin treatment device to ensure that the position and/or the radius of curvature of the wave front is within the prescribed range of the sensed position and/or sensed radius of curvature of the maximally curved protrusion. Additionally or alternatively, the curvature sensor may sense the height of the maximally curved protrusion in the aperture to ensure that the protrusion is located at the right location. Using such a curvature sensor may enable a single indenter to be used for different skin types, because variations in the position and/or the curvature may be measured and, possibly, corrected by the skin treatment device. Such a curvature sensor may be selected from a list comprising an optical sensor, a capacitive sensor, and a reflected light sensor. Any of these sensors may be used to determine the position and/or the radius of curvature of the maximally curved protrusion. The optical sensor may, for example, generate a low-power laser beam substantially perpendicular to the optical axis of the skin treatment device to sense a height of the maximally curved protrusion above the skin contact surface. Also a capacitive sensor may be used to determine a position of the maximally curved protrusion in the aperture, as the capacitive signal produced by the capacitive sensor changes when a distance between the capacitive sensor and the skin surface changes. The capacitive sensor may, for example, also be curved, and thus the capacitive sensor may also provide information about the quality of the curvature of the maximally curved protrusion derived from the capacity measurement. The curvature sensor may, for example, be configured for focusing reflected treatment light, which is reflected from the skin surface of the maximally curved protrusion, onto a detector. The intensity of the reflected treatment light may be dependent on the quality of the curvature of the maximally curved protrusion, and a feedback signal from the detector may be used to adapt the pressure or a cross-sectional dimension of the aperture or, alternatively, the focus position as generated by the optical system to ensure that the radius of the curvature of the wave front of the treatment light at the skin surface of the maximally curved protrusion corresponds, within the prescribed tolerance range, to the curvature of the skin surface of the maximally curved protrusion. Especially the adjustment of the focus position may be done relatively easily, and thus the skin treatment device may be used for different skin types without changing the indenter. Instead, the focus of the optical system is adjusted such that the radius of the curvature of the wave front matches, within the prescribed tolerance range, the radius of curvature of the maximally curved protrusion which is generated by pressing the indenter against the skin surface.

In an embodiment of the skin treatment device, the optical system is configured for adapting a location of the focus position inside the skin tissue in response to a signal from the curvature sensor. As mentioned hereinbefore, such a signal from the curvature sensor may be a feedback signal which allows the optical system to adapt the focus position inside the skin tissue such that the radius of curvature of the wave front of the focused treatment light at the surface of the curved protrusion coincides, within the prescribed tolerance range, with the radius of curvature of the maximally curved protrusion. If the signal from the curvature sensor indicates that the actual curvature of the protrusion differs too much from the curvature of the wave front, such that it cannot be corrected by adapting the focus position inside the skin tissue, the skin treatment device may, for example, provide a visible or audible signal to the user and possibly suggest changes to the skin treatment device to ensure that the treatment may still be carried out. Such suggestions may, for example, include a suggestion to replace the indenter by a different indenter which is able to create a maximally curved protrusion which may be corrected using the optical system.

In an embodiment of the skin treatment device, the aperture has a circular, elliptical, square, rectangular or polygonal shape. Especially by using a circular aperture, an equilateral triangular aperture, a square aperture or another polygonal aperture which is symmetric with respect to the optical axis of the treatment light beam, the shape of the surface of the maximally curved protrusion at the intersection with the optical axis is substantially a dome shape, which enables substantially three-dimensional matching of a curved shape of the wave front of the focused treatment light beam with said dome shape by virtue of such a circular or polygonal aperture. This results in optimal focusing of the treatment light into the skin tissue and in a very low spherical aberration. In an embodiment of the skin treatment device, the aperture comprises a circumferential edge having a radius of curvature in a range between 25 micrometer and 200 micrometer, preferably between 50 micrometer and 150 micrometer. In a further embodiment of the skin treatment device, a skin contact surface of the indenter is composed of non-corrosive material. In a further embodiment of the skin treatment device. The treatment light has a wavelength in a range between 350 nanometer and 10 micrometer, preferably in a range between 400 nanometer and 3 micrometer.

It should be noted that items, which have the same reference numbers in different Figures, have the same structural features and the same functions, or constitute the same signals. Where the function and/or structure of such an item have been explained, there is no necessity for repeated explanation thereof in the detailed description.

DETAILED DESCRIPTION OF EMBODIMENTS

Figure 1:
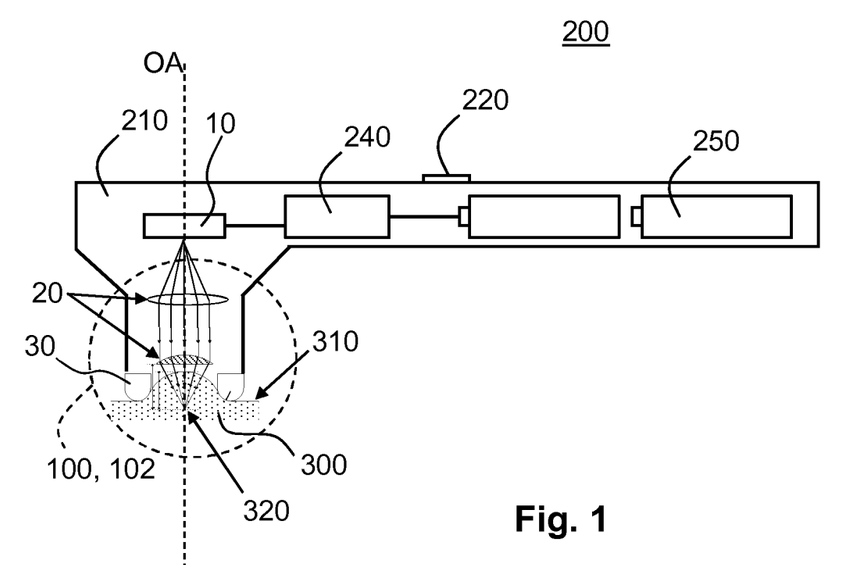
FIG. 1 diagrammatically shows an embodiment of the skin treatment device according to the invention, FIG. 2 diagrammatically shows a first embodiment of an indenter construction for the skin treatment device according to the invention, FIG. 3 diagrammatically shows a second embodiment of an indenter construction for the skin treatment device according to the invention.

FIG. 1 diagrammatically shows an embodiment of the skin treatment device 200 according to the invention. The skin treatment device 200 according to the invention comprises a housing 210 which comprises, for example, a controller 240, connection elements (not shown) for connecting the control circuits and power means 250 such as batteries or a connection to a mains power supply (not shown). Furthermore, the skin treatment device 200 typically comprises a switch 220 such as an on/off switch of the skin treatment device 200. Also a light source 10 is indicated in the skin treatment device 200 as shown in FIG. 1, which may, for example, comprise a laser light source 10 for generating the treatment light 15 (see FIG. 2). Alternatively, the light source 10 may be an output window of a fiber glass conduit (not shown) arranged to transport the treatment light 15 from a remote light source (not shown) to the optical system 20 such that the optical system 20 focuses the treatment light 15 along the optical axis OA into the skin tissue 300 when in use. Also present in the skin treatment device 200 according to the invention is an indenter construction 100, 102 which, in the shown embodiment, comprises a part of the optical system 20 and the indenter 30. In use, the skin treatment device 200 is pressed against the skin surface 310 at a pressure exceeding the predefined pressure, to generate a maximally curved protrusion 330 (see FIG. 2) for enhancing the optical system's 20 focusing quality of the treatment light 15 toward the focus position 320 in the skin tissue 300.

Figure 2:
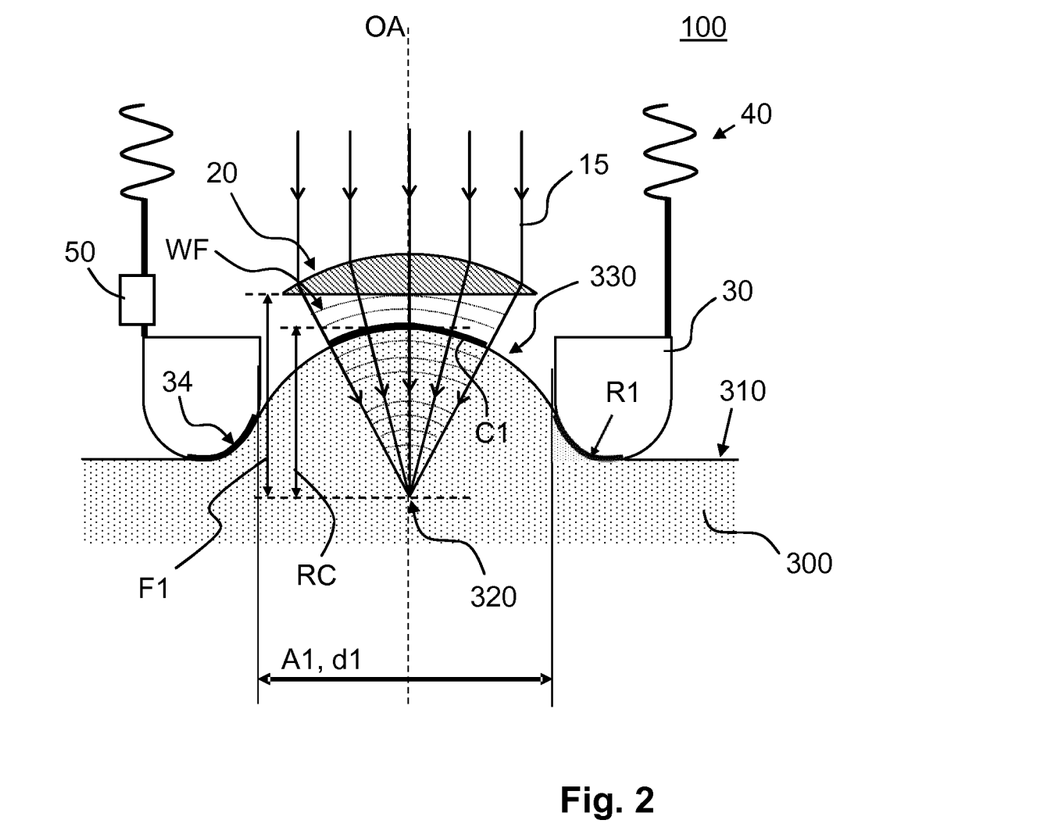

FIG. 2 diagrammatically shows a first embodiment of an indenter construction 100 for the skin treatment device 200 according to the invention. FIG. 2 shows part of the optical system 20 focusing the treatment light 15 into the skin tissue 300. Also shown are the wave fronts WF of the focused treatment light 15 as the focused treatment light 15 progresses towards the skin surface 310 of the curved protrusion 330 freely protruding inside the aperture A1. When the pressure at which the indenter 30 is pressed against the skin surface 310 exceeds the predefined pressure, the radius of curvature RC of the curved skin surface of the curved protrusion 330 freely protruding inside the aperture A1 having a specific width dimension d1 for a specific skin type is well defined, said curved protrusion constituting a maximally curved protrusion 330. The optical system 20 is configured and arranged to focus the treatment light 15 such as to generate a wave front WF at the skin surface 310 of the maximally curved protrusion 330 near the optical axis OA, and particularly at the intersection of the optical axis OA and the surface of the maximally curved protrusion 330. In this embodiment, a radius of the curvature of the wave front WF of the focused treatment light 15 substantially corresponds to the radius of curvature of the maximally curved protrusion 330. In such a situation, the disturbance of the wave front WF of the treatment light 15 when entering the skin tissue 300 is relatively low and hence the focus position 320 inside the skin tissue 300 is relatively well defined.

To ensure that the radius of curvature of the wave front WF substantially matches the radius of curvature RC of the maximally curved protrusion 330, at the surface of the curved protrusion 330 and in particular at the intersection of the optical axis OA and said surface, a distance between the focus position 320 inside the skin tissue 300 and the surface of the maximally curved protrusion 330 should be substantially equal to the radius of curvature RC of the maximally curved protrusion 330. Consequently, the focus position 320 inside the skin tissue 300 should substantially match a center of the circle fitted to the radius of curvature RC of the maximally curved protrusion 330. Next, a distance between the optical system 20 and the skin contact surface 34 of the indenter 30 and the focal distance µl of the optical system 20 should be selected such that the focus position 320 of the optical system 20 substantially coincides with the center of the circle fitted to the radius of curvature RC.

In FIG. 2 only a cross-section of the aperture A1 is shown. As mentioned hereinbefore, the aperture A1 may be an elongated aperture, for example, elongated in a direction transverse to the drawn cross-section of FIG. 2. In such an embodiment, the optical system 20 may, for example, focus the treatment light 15 in an elongated focus line into the skin tissue 300, wherein the wave front WF of such an elongated focus line substantially matches the shape of the elongated protrusion generated by the elongated aperture. Alternatively, the optical system 20 may generate an array of treatment spots (not shown) which are all focused, through the single elongated aperture, in the skin tissue 300. In such an embodiment, the radius of curvature of the wave front WF of the treatment light 15 focused in the array of treatment spots only substantially corresponds to the radius of curvature of the curved protrusion 330 in one direction of the aperture A1. Although in such a situation some residual spherical aberration would be present, the matching of the radius of curvature of the wave front WF and the radius of curvature RC of the maximally curved protrusion in one direction would already improve the overall imaging quality of the skin treatment device 200 according to the invention. When using a symmetric aperture A1, which is symmetric with respect to the optical axis OA, the curved protrusion 330 at the optical axis OA is substantially dome-shaped, enabling a substantially three-dimensional match of the curvature of the wave front WF and the curvature RC of the curved protrusion 330. Such an aperture may, for example, be a circular aperture A1, an equilateral triangular aperture A1, a square aperture A1 or another symmetric polygonal aperture A1. This would result in optimal focusing of the treatment light 15 into the skin tissue 300 and in a very low spherical aberration.

The indenter construction 100 as shown in FIG. 2 further comprises a resilient element 40. Such a resilient element 40 may be used to ensure that the pressure with which the indenter 30 is applied to the skin surface 310 exceeds the predefined pressure. For example, the skin treatment device 200 may be pressed against the skin surface 310 until, for example, a length of the resilient element 40 is at least partially reduced due to the applied pressure. If this happens, the applied pressure exceeds the predefined pressure against the skin surface 310. A further benefit when using such a resilient element 40 is that it ensures that always substantially the same pressure is applied during the treatment using the skin treatment device 200. For example, when the resilient element 40 is a spring 40, the pressure may be increased until the spring 40 shortens, but not until the spring 40 is completely compressed. This ensures that the pressure with which the indenter 30 is applied to the skin surface 310 is always substantially the same.

In addition or alternatively to the resilient element 40, the indenter construction 100 may comprise a pressure sensor 50. The pressure sensor 50 may, for example, ensure that, in use, the pressure applied by the indenter 30 against the skin surface 310 exceeds the predefined pressure. The pressure sensor 50 may sense an applied pressure and a controller 240 (see FIG. 1) may, for example, interpret this sensed pressure and act as a kind of activation button. As soon as the sensed pressure exceeds the predefined pressure, the controller 240 may activate the light source 10 to start the treatment. Alternatively, the controller 240 may, for example, generate a signal to the user audible or visible as soon as the pressure sensed by the pressure sensor 50 exceeds the predefined pressure such that the light-based treatment may be initiated. Such a pressure sensor 50 may, for example, be a piezoelectric sensor 50, but any other suitable pressure sensor 50 may be used. A further benefit of having the pressure sensor 50 in the skin treatment device 200 according to the invention is that different predefined pressure levels may be used for different indenters 30, 32 (see FIG. 3) of the skin treatment device 200. The controller 240 and/or pressure sensor 50 may be manually set to a different level when use is made of a different indenter 30, 32 or when the indenter 30 is used at a different skin type. Alternatively, the skin treatment device may recognize the indenter 30 for example, via any type of known wired or wireless identification mechanism and use a different predefined pressure level automatically, for example, by looking up the corresponding or required predefined pressure level from a further look-up table (not shown) indicating the required pressure levels for different skin types and different indenters 30, 32.

Figure 3:
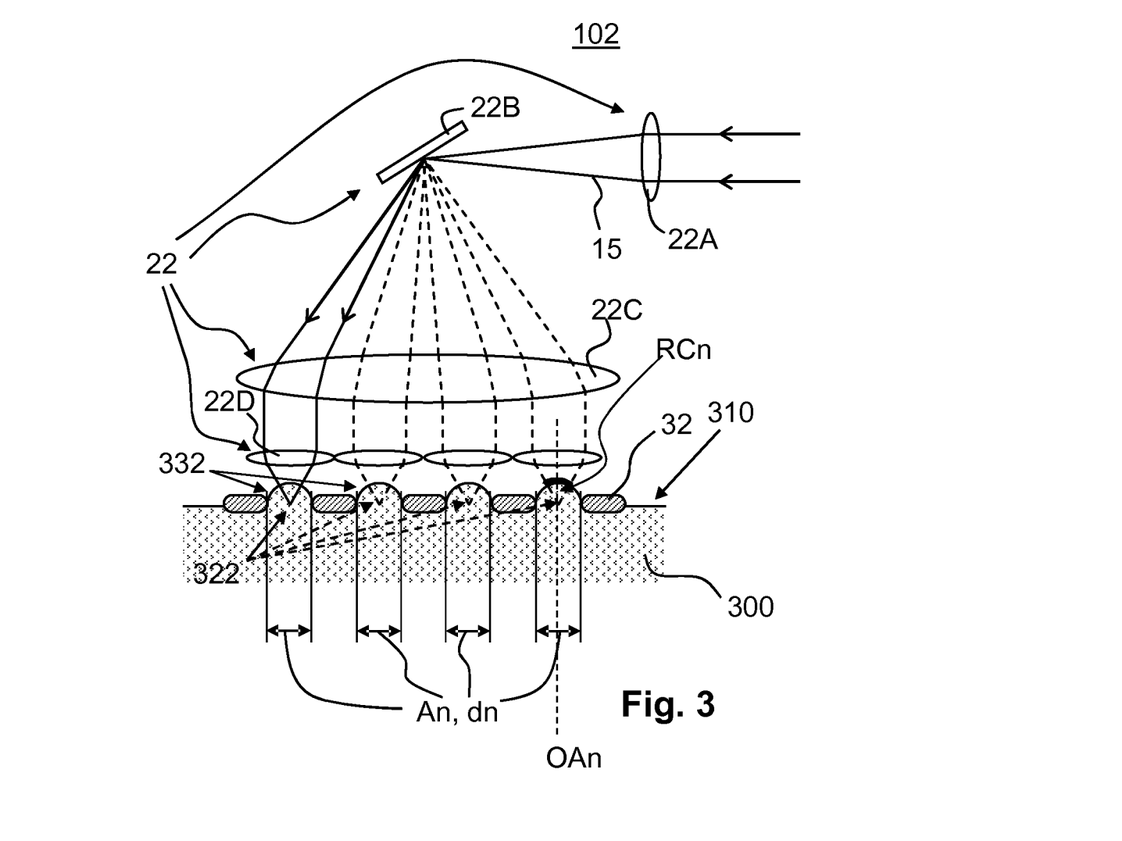

FIG. 3 diagrammatically shows a second embodiment of the indenter construction 102 for the skin treatment device 200 according to the invention. In this embodiment, the optical system 22 is constructed to generate a plurality of spatially separate focusing positions 322 inside the skin tissue 300. In the embodiment shown in FIG. 3, the optical system 22 comprises a first optical element 22A for focusing the treatment light 15 from, for example, a laser light source 10 (not shown) to a moving mirror 22B which sequentially redirects the treatment light 15, via a projection lens 22C, to individual different focusing lenses 22D in an array of focusing lenses 22D. Each of the different focusing lenses 22D focuses the treatment light 15 along the individual optical axis OAn into the skin tissue 300 to the individual focusing positions 322. A benefit of this sequential focusing of the treatment light 15 into the different focusing positions 322 is that the intensity of the treatment light 15 required for the light-based skin treatment is relatively low as all treatment light 15 is sequentially focused into the plurality of focusing positions 322. In an alternative embodiment, the mirror 22B may be a static mirror 22B and the first optical element 22A may spread the treatment light 15 via the static mirror 22B across the projection lens 22C. This projection lens 22C spreads the treatment light 15 across the array of focusing lenses 22D such that the light is simultaneously focused into the individual focusing positions 322 inside the skin tissue 300.

The indenter 32 comprises a plurality of apertures An, each having a predefined cross-sectional width dimension dn for generating a plurality of curved protrusions 332 freely protruding from the skin surface 310 into the individual apertures An. Each of the plurality of apertures An is configured and constructed for generating a maximally curved protrusion 332 inside the individual apertures An when the indenter 32 is pressed at the pressure exceeding the predefined pressure. Each radius of curvature RCn of the maximally curved protrusions 332 substantially coincides with the radius of curvature of the wave front WF (not shown) of the treatment light 15 as focused into the associated focus positions 322 by the optical system 22. A benefit of this embodiment is that multiple positions inside the skin tissue 300 may be treated at the same time by the skin treatment device 200. Especially when the width dimension of the cross-sections dn of the aperture An is less than 2 millimeter, the skin treatment device 200 may relatively easily comprise a plurality of apertures An to ensure this simultaneous treatment. The plurality of apertures An may be arranged in a one-dimensional array or a two-dimensional array (not shown). Furthermore, the skin treatment device 200 may comprise different indenters 32, wherein a distance between two neighboring apertures An is different for the different indenters 32. By choosing a specific indenter 32, a user may choose a density of focusing positions 322 inside the skin tissue 300. Differences in density of the focusing positions 322 may be preferred for some specific light-based treatments of the skin tissue 300.

Also when the indenter 32 is used having a plurality of focusing positions 322 inside the skin tissue 300, resilient elements 40 (not shown) and a pressure sensor 50 (not shown) as explained in relation to FIG. 2 may be used here as well, leading to the same or similar advantages.

Figure 4:
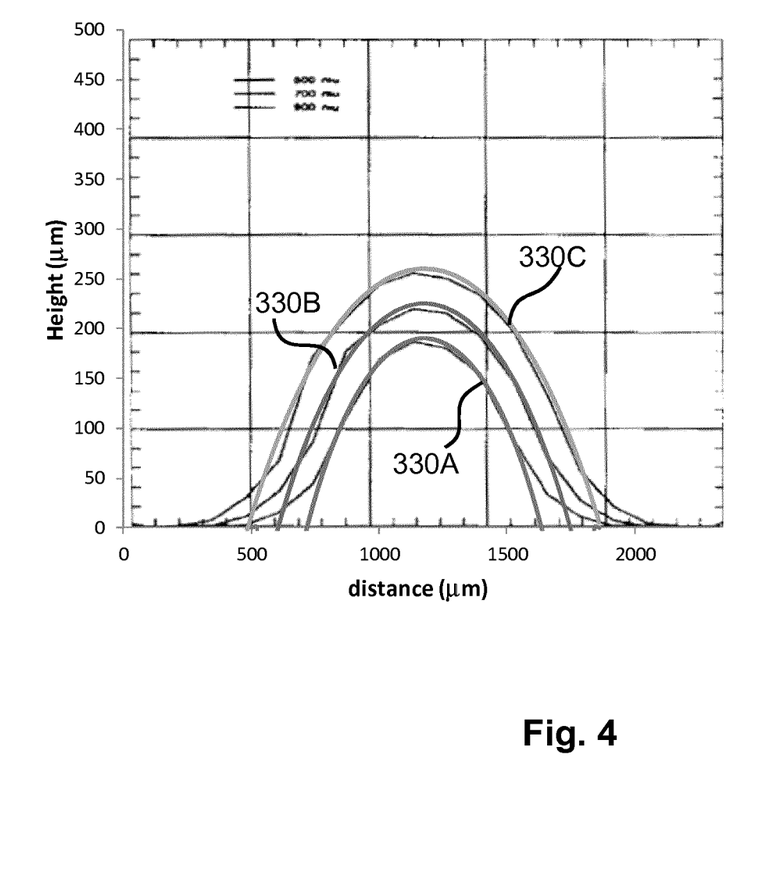
FIG. 4 shows experimental results of curvature profiles of curved protrusions for different cross-sectional width dimensions of the aperture of the indenter.

FIG. 4 shows experimental results of curvature profiles of curved protrusions 330A, 330B, 330C for different aperture cross-sectional width dimensions d1, dn. The solid lines overlaying the experimental measurements are fitted curves to identify the maximally curved protrusions 330 (not shown) for the different aperture cross-sections. The innermost solid line represents a curved protrusion 330A resulting from a circular aperture d1 having a cross-sectional width dimension of 500 micrometers. The middle solid line represents a curved protrusion 330B resulting from a circular aperture d1 having a cross-sectional dimension of 700 micrometer. The outer solid line represents a curved protrusion 330C resulting from a circular aperture d1 having a cross-sectional dimension of 900 micrometer.

Figure 5:
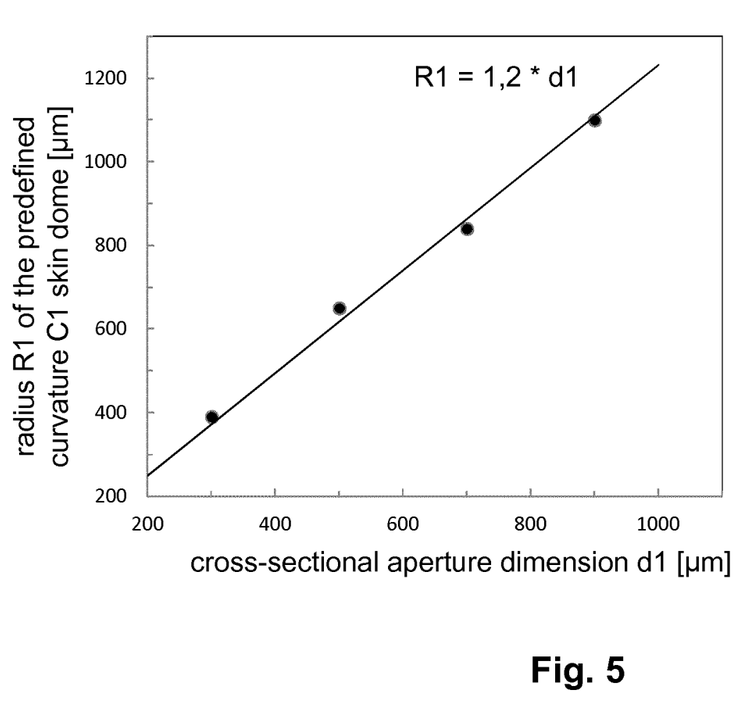
FIG. 5 shows a relation between the radius of curvature of the curved protrusion and the cross-sectional width dimension of the aperture, and FIG. 6 diagrammatically shows an embodiment of a curvature sensor according to the invention.

FIG. 5 shows a relation between the radius of curvature RC (see FIG. 2) of the curved protrusion 300 and the cross-sectional width dimension d1 of the aperture. The graph in FIG. 5 shows, on the horizontal axis, different cross-sectional width dimensions d1 of the aperture in micrometers and, on the vertical axis, the radius of curvature RC of the maximally curved protrusion 330 in micrometers. Again, the aperture A1 used for the experimental data is a circular aperture A1 and the maximally curved protrusions 330 generated by the circular aperture A1 is a dome-shaped protrusion. The data is obtained from one specific skin type being human facial skin at the cheek of the face. As can be seen from the graph shown in FIG. 5, the relation between the cross-sectional width dimension d1 of the aperture and the radius of curvature RC of the maximally curved skin protrusion created for a specific skin type, when using a pressure exceeding the predefined pressure, is a substantially linear relation according to RC=1,2*d1.

Figure 6:
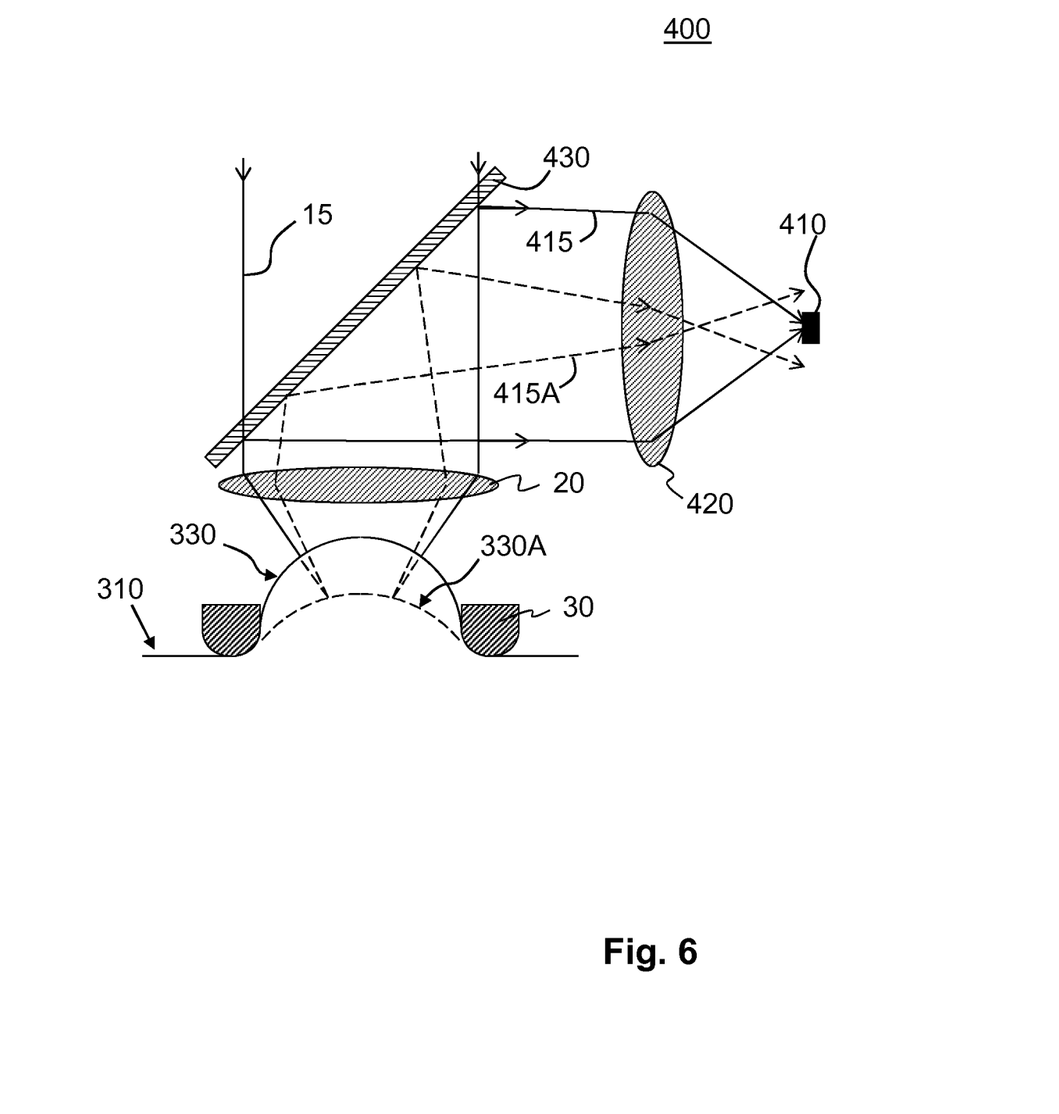

FIG. 6 diagrammatically shows an embodiment of a curvature sensor 400 according to the invention. FIG. 6 shows a part of the optical system 20 and of the indenter 30 of the skin treatment device 200 according to the invention. As illustrated in FIG. 6, the indenter 30 is pressed against the skin surface 310 to create a curved protrusion 330, 330A. If the curvature of the curved protrusion substantially corresponds to the maximally curved protrusion 330, the radius of curvature of the wave front (not shown) of the treatment light 15 at the location of the maximally curved protrusion substantially coincides with the radius of curvature RC of the maximally curved protrusion. This results in relatively limited spherical aberrations when the treatment light 15 is focused into the skin tissue 300. The embodiment of the curvature sensor 400 as shown in FIG. 6 comprises a semi-transparent mirror 430 for reflecting reflected treatment light 415, 415A via a focusing optics 420 onto a detector 410 for detecting an intensity of the reflected treatment light 415, 415A. In a first situation, the curvature of the curved protrusion 330A is not correct, so that the curvature of the wave front (not shown) as created by the optical system 20 does not correspond to the curvature of the curved protrusion 330A. In such a situation, the reflected treatment light 415A, indicated with dashed lines, is not focused onto the detector 410 and hence the intensity measured by the detector 410 is relatively low. This may be caused by the fact that the aperture A1 of the indenter 30 does not correctly match the skin type of the skin tissue 300 on which the skin treatment device 200 is used or because the pressure at which the indenter 30 is applied against the skin does not exceed the predefined pressure. To correct for this, a user may select a different indenter 30 having a different aperture A1 to produce a different curved protrusion 300. The reflected treatment light 415 which originates from the adapted curved protrusion 300 is indicated with a solid line 415 which is focused by the focusing optics 420 of the curvature sensor 400 onto the sensor 410, causing the intensity of the detector 410 to be relatively high, which indicates that the curvature of the wave front of the focused treatment light 15 substantially corresponds to the maximally curved protrusion 330.

As mentioned hereinbefore, instead of replacing the indenter 30, also the focus characteristics of the optical system 20 of the skin treatment device 200 according to the invention may be adapted in dependence on a signal received from the detector 410 of the curvature sensor 400. As such, the generated curved protrusion 330 will remain the same, but the focus position 320 (see FIG. 2) inside the skin tissue 300 will be changed such that the radius of curvature of the wave front WF (see FIG. 2) matches the radius of curvature RC of the curved protrusion 330 (see FIG. 2).

In summary, the invention provides a non-invasive skin treatment device 200 comprising: a light source 10 constructed for emitting treatment light 15, an optical system 20 constructed for focusing the treatment light along an optical axis OA to a focus position 320 inside the skin tissue 300, and an indenter 30 comprising a skin contact surface 34 having an aperture A1 at a distance from the optical system for allowing the treatment light to be focused through the aperture into the skin tissue. The indenter is configured and constructed for generating, in a cross-section of the aperture taken along the optical axis and along a cross-section direction wherein the aperture has a width dimension, a maximally curved protrusion of skin tissue freely protruding through the aperture towards the optical system by pressing the indenter against the skin surface of a specific skin type with a pressure exceeding a predefined pressure, a skin surface of said maximally curved protrusion having a radius of curvature RC at an intersection with the optical axis. The optical system is configured and constructed for generating a focused beam of the treatment light having, in said cross-section of the aperture at said intersection, a wave front with a radius of curvature ranging between 75% and 125% of said radius of curvature RC of the skin surface of said maximally curved protrusion.

It should be noted that the above-mentioned embodiments illustrate rather than limit the invention, and that those skilled in the art will be able to design many alternative embodiments.

In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A skin treatment device for light-based treatment of skin tissue, the skin treatment device comprising:
    a light source constructed for emitting treatment light,
    an optical system constructed for focusing the treatment light along an optical axis (OA, OAn) to a focus position inside the skin tissue, and
    an indenter comprising a skin contact surface having an aperture (A1, An) at a distance from the optical system for allowing the treatment light to be focused through the aperture (A1, An) into the skin tissue, the indenter and the aperture (A1, An) being configured and constructed for generating, in a cross-section of the aperture (A1, An) taken along the optical axis (OA, OAn) wherein the aperture (A1, An) has a width dimension (d1, dn), a maximally curved protrusion of skin tissue freely protruding through the aperture (A1, An) towards the optical system when the indenter is pressed against the skin surface with a pressure exceeding a predefined pressure above which the freely protruding curved protrusion remains constant, a skin surface of said maximally curved protrusion having a radius of curvature (RC, RCn) at an intersection with the optical axis (OA, OAn),
    the optical system being configured and constructed for generating a focused beam of the treatment light having, in said cross-section of the aperture (A1, An) at said intersection, a wave front (WF) with a radius of curvature being in a range between 75% and 125% of said radius of curvature (RC, RCn) of the skin surface of said maximally curved protrusion.

2. The skin treatment device according to claim 1, wherein said width dimension (d1, dn) of the aperture (A1, An) is less than 2 millimeter.

3. The skin treatment device according to claim 2, wherein the predefined pressure is 1.43 Newton per square centimeter.

4. The skin treatment device according to claim 1, wherein the radius of curvature of the wave front (WF) is in a range between 95% and 105% of said radius of curvature (RC, RCn) of the skin surface of the maximally curved protrusion.

5. The skin treatment device according to claim 1, wherein the indenter is removably attached to the skin treatment device and is replaceable by a further indenter having a further aperture different from the aperture (A1, An).

6. The skin treatment device according to claim 1, wherein said a dimension (d1, dn) of the aperture (A1, An) along the optical axis is larger than 2 millimeter.

7. The skin treatment device according to claim 1, wherein the optical system is configured and constructed to generate a plurality of spatially separate focusing positions inside the skin tissue, and wherein the indenter comprises a plurality of apertures (An) each associated with a respective one of said plurality of focusing positions and each configured and constructed for generating a maximally curved protrusion of the skin tissue, the optical system being configured and constructed for generating a plurality of focused beams of the treatment light each having, in said cross-section of the associated aperture (A1, An) at said intersection, a wave front (WF) with a radius of curvature being in a range between 75% and 125% of said radius of curvature (RCn) of the skin surface of said maximally curved protrusion.

8. The skin treatment device according to claim 1, wherein the indenter is attached to the skin treatment device via a resilient element.

9. The skin treatment device according to claim 1, wherein the skin treatment device comprises a pressure sensor for measuring the pressure with which the indenter, in use, is pressed against the skin surface, and a control circuit configured to control the light source to emit the treatment light only when the pressure measured by the pressure sensor exceeds the predefined pressure.

10. The skin treatment device according to claim 1, wherein the skin treatment device further comprises a curvature sensor for sensing a position and/or a curvature of the maximally curved protrusion at the intersection with the optical axis (OA, OAn).

11. The skin treatment device according to claim 10, wherein the curvature sensor is selected from a list comprising: optical sensor, capacitive sensor, reflected light sensor.

12. The skin treatment device according to claim 10, wherein the optical system is configured for adapting a location of the focus position inside the skin tissue in response to a signal from the curvature sensor.

13. The skin treatment device according to claim 10, wherein the curvature sensor is configured for focusing reflected treatment light, which is reflected from the skin surface of the maximally curved protrusion, onto a detector.

14. The skin treatment device according to claim 1, wherein the aperture (A1, An) has a circular, elliptical, square, rectangular or polygonal shape.

15. The skin treatment device according to claim 1, wherein the aperture (A1, An) comprises a circumferential edge having a radius of curvature (R1) in a range between 25 micrometer and 200 micrometer.

16. The skin treatment device according to claim 1, wherein the treatment light has a wavelength in a range between 350 nanometer and 10 micrometer.

* * * * *